United States Patent
Maeda (10) Patent No.: US 10,564,136 B2
(45) Date of Patent: Feb. 18, 2020

(54) LIQUID SAMPLE ANALYSIS SYSTEM

(71) Applicant: SHIMADZU CORPORATION, Kyoto-shi, Kyoto (JP)

(72) Inventor: Kazuma Maeda, Kyoto (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 0 days.

(21) Appl. No.: 15/780,829

(22) PCT Filed: Dec. 4, 2015

(86) PCT No.: PCT/JP2015/084112
§ 371 (c)(1),
(2) Date: Jun. 1, 2018

(87) PCT Pub. No.: WO2017/094178
PCT Pub. Date: Jun. 8, 2017

(65) Prior Publication Data
US 2018/0372696 A1  Dec. 27, 2018

(51) Int. Cl.
*G01N 30/00* (2006.01)
*G01N 30/72* (2006.01)
(Continued)

(52) U.S. Cl.
CPC ........ *G01N 30/724* (2013.01); *H01J 49/0445* (2013.01); *H01J 49/107* (2013.01);
(Continued)

(58) Field of Classification Search
USPC .......................................................... 250/288
See application file for complete search history.

(56) References Cited

U.S. PATENT DOCUMENTS 5,703,360 A    12/1997  Fischer et al.
7,462,821 B2 * 12/2008  Barket, Jr. .......... H01J 49/0031
                                                      250/281
(Continued)

FOREIGN PATENT DOCUMENTS

WO    2006/107831 A2    10/2006

OTHER PUBLICATIONS

Extended European Search Report dated Nov. 30, 2018 issued by the European Patent Office in counterpart application No. 15909808.6.

*Primary Examiner* — Phillip A Johnston
(74) *Attorney, Agent, or Firm* — Sughrue Mion, PLLC (57) ABSTRACT

A liquid sample analyzing system including an ion analyzer having a first ion source receiving a target sample and a second ion source receiving a reference sample; a liquid sample introduction mechanism 3 including a passage-switching section introducing reference samples into the second ion source; and a controller for repeatedly performing a series of steps in the ion analyzer, the steps including: a pre-measurement step for initiating a measurement; a measurement step for introducing a target sample into the first ion source and performing a measurement on an ion originating from the target sample along with an ion originating from a reference sample introduced into the second ion source by the liquid sample introduction mechanism; and a post-measurement step where the liquid sample introduction mechanism operates concurrently with the predetermined post-measurement step to switch the passage-switching section to a passage having a reference sample for the next analysis.

13 Claims, 4 Drawing Sheets

(51) Int. Cl.
*H01J 49/10* (2006.01)
*H01J 49/04* (2006.01)
*G01N 30/02* (2006.01)
*G01N 30/62* (2006.01)

(52) U.S. Cl.
CPC ... *G01N 30/7273* (2013.01); *G01N 2030/027* (2013.01); *G01N 2030/626* (2013.01); *H01J 49/044* (2013.01)

(56) References Cited

U.S. PATENT DOCUMENTS

| | | | | |
|---|---|---|---|---|
| 8,800,352 | B2* | 8/2014 | Marks | G01N 30/24 73/61.55 |
| 8,809,768 | B2* | 8/2014 | Bateman | H01J 49/0031 250/281 |
| 10,186,410 | B2* | 1/2019 | Eiler | H01J 49/0009 |

* cited by examiner

LIQUID SAMPLE ANALYSIS SYSTEM

TECHNICAL FIELD

The present invention relates to a liquid sample analyzing system which includes an ion analyzer for ionizing and analyzing a liquid sample to be analyzed as well as a liquid sample introduction mechanism capable of selectively introducing a plurality of kinds of liquid samples into the ion analyzer.

BACKGROUND ART

A liquid chromatograph mass spectrometer is one type of device for analyzing components contained in a liquid sample. In the liquid chromatograph mass spectrometer, the components in a liquid sample are temporally separated from each other through a column in the liquid chromatograph and sequentially introduced into the mass spectrometer. Each component in the liquid sample introduced into the mass spectrometer is ionized by an ion source, and the generated ions are separated from each other according to their mass-to-charge ratios.

Some mass spectrometers include another ion source into which a reference liquid sample from which an ion having known mass-to-charge ratio will be generated ("second ion source"), in addition to the ion source into which the liquid sample to be analyzed is introduced from the liquid chromatograph ("first ion source"). When such a mass spectrometer is used, mass calibration of the measurement data can be performed by detecting the ion originating from the reference liquid sample along with the ions originating from the liquid sample to be analyzed. In the case of analyzing an unknown liquid sample, it is normally necessary to prepare a plurality of kinds of different reference samples. Additionally, in the case of performing a quantitative measurement of the components in the liquid sample to be analyzed, it is necessary to prepare a plurality of kinds of reference samples which have been adjusted at known concentrations which differ from each other.

For example, a liquid sample introduction mechanism described in Patent Literature 1 is used to selectively introduce one of the plurality of reference liquid samples into the second ion source of the mass spectrometer. This mechanism includes: a passage-switching section having a plurality of sub-ports and a main port to be connected to one of the sub-ports in a switchable manner; and first liquid supply passages, each of which has one end connected to one of a plurality of liquid sample containers holding reference liquid samples and the other end connected to one of the sub-ports; and a second liquid supply passage connecting the main port and the second ion source of the mass spectrometer. With this liquid sample introduction mechanism, a reference liquid sample which is the most suitable for the liquid sample to be analyzed among the plurality of reference liquid samples can be selectively introduced into the second ion source.

A flow of an analysis performed in the liquid sample analyzing system including the previously described liquid sample introduction mechanism and a liquid chromatograph mass spectrometer is as follows:

Initially, in the liquid chromatograph mass spectrometer, an analysis controller for controlling the analyzing operation of each section of the liquid chromatograph mass spectrometer makes each section shift into a state for initiating the measurement based on the previously determined conditions for the execution of the analysis. Concurrently, in the liquid sample introduction mechanism, the passage-switching section is switched to introduce a specific kind of reference liquid sample through the second liquid-supply passage into the second ion source.

After the previously described operations have been completed in both the liquid chromatograph mass spectrometer and the liquid sample introduction mechanism, a liquid sample to be analyzed is introduced into the liquid chromatograph under the control of the analysis controller. The components temporally separated from each other by the column of the liquid chromatograph are sequentially introduced into the first ion source of the mass spectrometer. Ions are generated from both the component in the liquid sample as the analysis target introduced into the first ion source and a reference liquid sample introduced into the second ion source. Those ions are separated from each other according to their mass-to-charge ratios, and the intensity of the ions is measured at each mass-to-charge ratio.

After the completion of the measurement, the data obtained through the measurement are subjected to a predetermined post-measurement-completion process in the liquid chromatograph mass spectrometer, such as the process of adding a header for identifying the analysis to the obtained data and storing those data in a predetermined file format, or the process of detecting a peak in a chromatogram or mass spectrum.

CITATION LIST

Patent Literature

Patent Literature 1: U.S. Pat. No. 5,703,360 B

SUMMARY OF INVENTION

Technical Problem

In recent years, ion analyzers, such as the liquid chromatograph mass spectrometer, have been used for analyses of a wide variety of targets, such as foodstuffs, drugs and biological samples. In those analyses, many specimens are exhaustively analyzed. Therefore, there is constant demand for reducing the analyzing time and enhancing the throughput of the analysis.

A liquid chromatograph mass spectrometer has thus far been used as one example of the device for generating ions from a liquid sample to be analyzed and performing an analysis of those ions. The reduction of the analyzing time and the enhancement of the throughput of the analysis have also been similarly demanded in a liquid sample analyzing system in which a different type of ion analyzer (e.g. an ion mobility spectrometer) is combined with a liquid sample introduction mechanism.

The problem to be solved by the present invention is to reduce the analyzing time and enhance the throughput of the analysis in a liquid sample analyzing system which includes an ion analyzer for ionizing and analyzing a liquid sample to be analyzed as well as a liquid sample introduction mechanism for selectively introducing a plurality of reference liquid samples into an ion source of the ion analyzer.

Solution to Problem

For example, in a liquid sample introduction mechanism for selectively introducing a plurality of liquid samples, the passage in the passage-switching section is switched to introduce a specific kind of reference liquid sample into the second ion source in a pre-measurement step. These operations require approximately a minimum of ten seconds. By comparison, a pre-measurement step for the liquid chromatograph mass spectrometer is normally completed within a shorter period of time. Therefore, in the conventional liquid sample analyzing system, the remaining time becomes a waiting time. Besides, in the liquid chromatograph mass spectrometer, the post-measurement-completion process mentioned earlier is performed as a post-measurement step, whereas there are normally fewer operations (or even no operation) performed as a post-measurement step in the liquid sample introduction mechanism. Therefore, in the conventional liquid sample analyzing system, a waiting time occurs in the liquid sample introduction mechanism.

The present inventor has discovered that a reduction of the analyzing time and an improvement in the throughput of the analysis can be achieved by making improvements in those aspects. Thus, the present invention has been conceived.

The present invention developed for solving the previously described problem is a liquid sample analyzing system used for continuously performing analyses of a plurality of liquid samples, including:

a) an ion analyzer including a first ion source into which a liquid sample to be analyzed is introduced and a second ion source into which a reference liquid sample is introduced;

b) a liquid sample introduction mechanism including a passage-switching section for selectively introducing a plurality of reference liquid samples into the second ion source; and c) an analysis controller for repeatedly performing a series of steps in the ion analyzer, the steps including: a pre-measurement step for making each section of the ion analyzer shift into a state for initiating a measurement; a measurement step for introducing a liquid sample to be analyzed into the first ion source and performing a measurement on an ion originating from the liquid sample along with an ion originating from a reference liquid sample introduced into the second ion source by the liquid sample introduction mechanism; and a post-measurement step for performing a predetermined post-measurement-completion process, where the analysis controller operates the liquid sample introduction mechanism concurrently with the predetermined post-measurement step so as to switch the passage-switching section to a passage through which a reference liquid sample to be used in a next analysis is introduced.

An example of the ion analyzer is a liquid chromatograph mass spectrometer.

Examples of the "predetermined post-measurement-completion process" include the process of adding a header for identifying the analysis to the obtained data and storing the data in a predetermined file format, and the process of extracting a peak from measurement data, such as a chromatogram or mass spectrum.

In the ion analyzer, a pre-measurement step for making each section of the ion analyzer shift into a state for initiating a measurement, and a post-measurement step for performing a predetermined post-measurement-completion process, are performed in addition to the measurement of a liquid sample to be analyzed. The post-measurement step normally requires a longer period of time than the pre-measurement step. On the other hand, the operation which primarily requires time in the liquid sample introduction mechanism is the operation of introducing a reference liquid sample into the second ion source. In the liquid sample analyzing system according to the present invention, the post-measurement step in the ion analyzer and the pre-measurement step (introduction of a standard reference sample) for the next analysis in the liquid sample introduction mechanism are concurrently performed. Since the time-consuming operations in the ion analyzer and the liquid sample introduction mechanism are concurrently performed, the waiting time in the present system will be shorter than in the conventional system.

Advantageous Effects of the Invention

With the liquid sample analyzing system according to the present invention, the analyzing time can be reduced, and the throughput of the analysis can be enhanced.

DESCRIPTION OF EMBODIMENTS

One embodiment of the liquid sample analyzing system according to the present invention is hereinafter described with reference to the drawings. The liquid sample analyzing system in the present embodiment has a configuration in which a liquid chromatograph mass spectrometer as the ion analyzer is combined with a liquid sample introduction mechanism capable of selectively introducing a plurality of reference liquid samples into the liquid chromatograph mass spectrometer.

Figure 1:
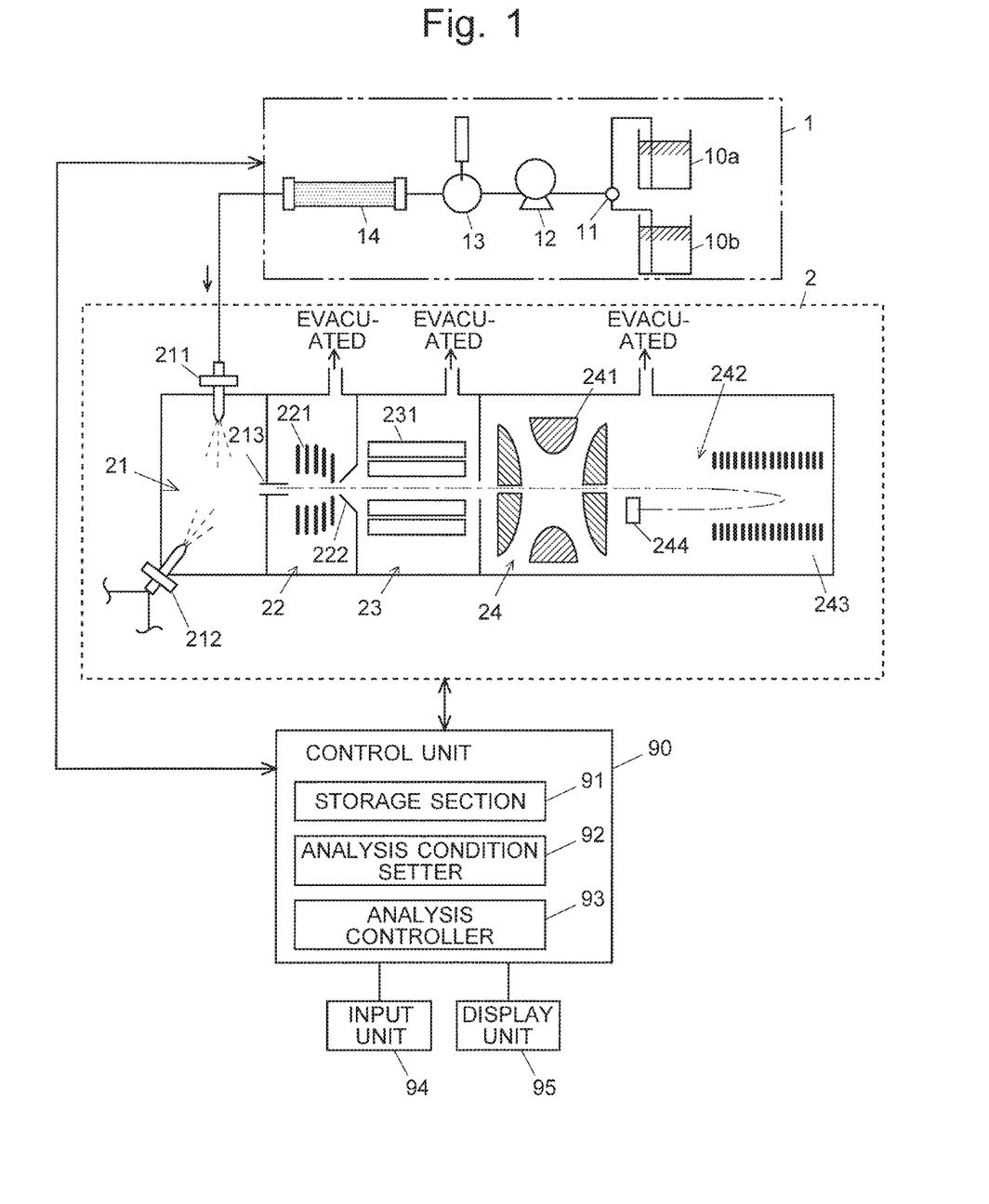
FIG. 1 is a configuration diagram of the main components in a liquid chromatograph unit, mass separator unit and control unit in one embodiment of the liquid sample analyzing system according to the present invention.

The liquid chromatograph unit (LC unit) 1 includes: mobile phase containers 10a and 10b in which two different kinds of mobile phases are stored; a mixer 11 for mixing the two mobile phases at a predetermined ratio; a pump 12 for drawing and supplying the mixed mobile phase at a fixed flow rate; an injector 13 for injecting a predetermined amount of sample liquid into the mobile phase; and a column 14 for temporally separating various kinds of compounds contained in the sample liquid. A plurality of liquid samples to be analyzed which are contained in an autosampler (not shown) are introduced into the injector 13 in a predetermined order and at a predetermined timing under the control of an analysis controller (which will be described later).

The mass spectrometer unit (MS unit) 2 includes an ionization chamber 21 maintained at atmospheric pressure and an analysis chamber 24 maintained in a high vacuum state by being evacuated with a vacuum pump (not shown). First and second intermediate vacuum chambers 22 and 23 having their degrees of vacuum increased in a stepwise manner are located between the ionization chamber 21 and the analysis chamber 24. The ionization chamber 21 communicates with the first intermediate vacuum chamber 22 through a thin desolvation tube 213. The first intermediate vacuum chamber 22 communicates with the second intermediate vacuum chamber 23 through a small orifice bored at the apex of a conical skimmer 222.

The various components in a liquid sample to be analyzed which have been temporally separated by the column 14 of the liquid chromatograph unit 1 are turned into electrically charged droplets by an ESI probe 211 and sprayed into the ionization chamber 21. Similarly, a reference liquid sample supplied from a liquid sample introduction mechanism 3 (which will be described later) is also transformed into electrically charged droplets by an ESI probe 212 and sprayed into the ionization chamber 21. Those charged droplets collide with gas molecules within the ionization chamber 21, being broken into even finer droplets, which are quickly dried (desolvated) and turned into ions. Due to the pressure difference between the ionization chamber 21 and the first intermediate vacuum chamber 22, those ions are drawn into the desolvation tube 213. Being converged by ion guides 221 and 231, the ions travel through the two intermediate vacuum chambers 22 and 23, to be introduced into a three-dimensional quadrupole ion trap 241 inside the analysis chamber 24.

In the ion trap 241, the ions are temporarily captured and stored by a quadrupole electric field created by radio-frequency voltages applied from a power source (not shown) to the electrodes. The various ions stored within the ion trap 241 are simultaneously given a specific amount of kinetic energy and thereby ejected from the ion trap 241 into a time-of-flight mass separator (TOF) 242. The TOF 242 includes reflectron electrodes 243, to which DC voltages are respectively applied from a DC power source (not shown). Due to the effect of the DC electric field created by those electrodes, the ions are returned and reach an ion detector 244. Among the ions which have been simultaneously ejected from the ion trap 241, an ion having a smaller mass-to-charge ratio flies at a higher speed. Accordingly, the ions arrive at the ion detector 244 with time differences depending on their mass-to-charge ratios. The ion detector 244 generates, as a detection signal, an electric current corresponding to the number of ions which have arrived at the detector. The output signals from the ion detector 244 are saved in a storage section 91 of a control unit 90 (which will be described later).

Figure 2:
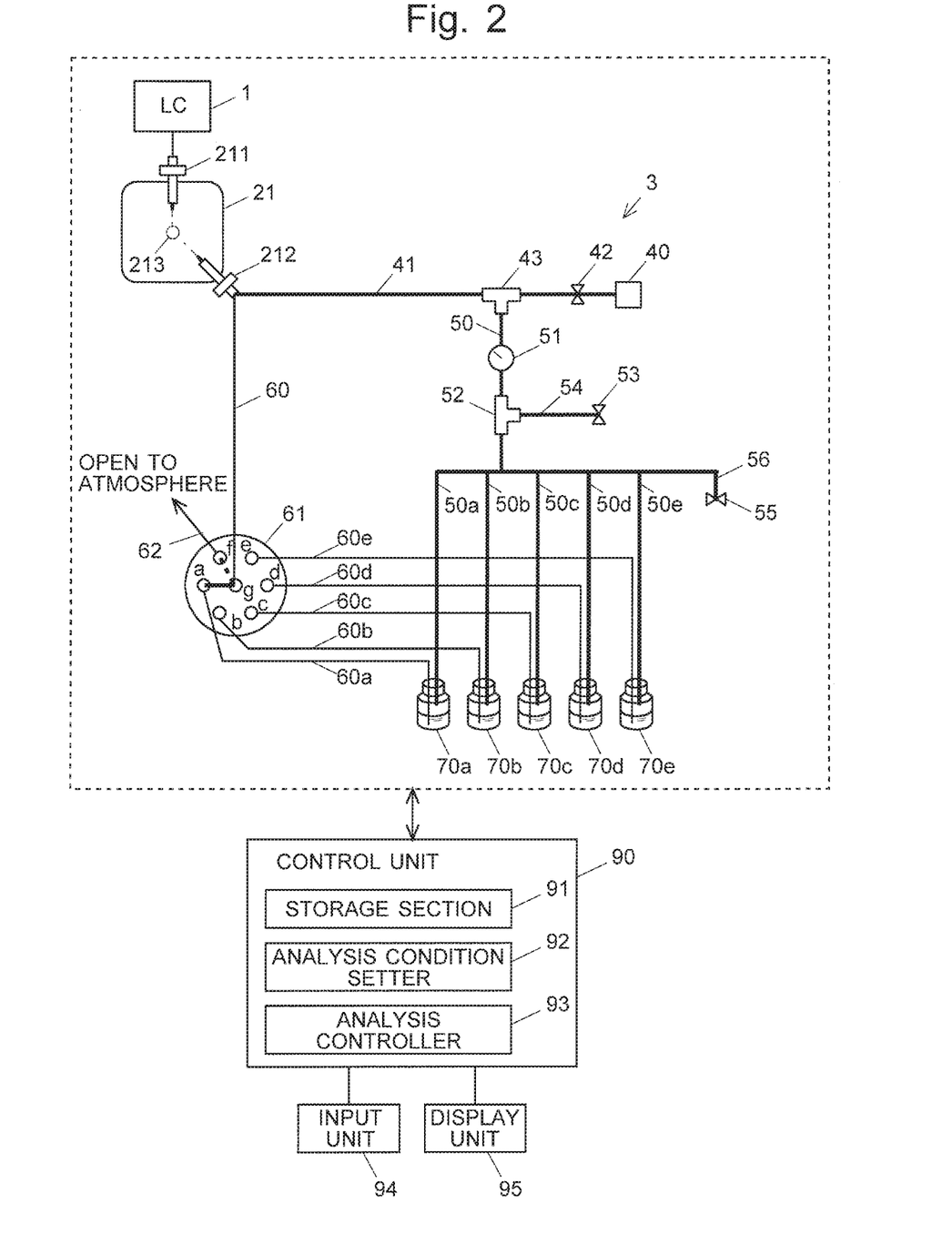
FIG. 2 is a configuration diagram of the main components in the liquid sample introduction mechanism and the control unit in the liquid sample analyzing system according to the present embodiment.

FIG. 2 shows the configuration of the main components of the liquid sample introduction mechanism (CDS) 3. The liquid sample introduction mechanism 3 is a mechanism for introducing a reference liquid sample for mass calibration into the ionization chamber 21 of the TOF-MS to ionize the reference liquid sample along with the liquid sample eluted from the column 14 of the liquid chromatograph unit 1. Five reference liquid samples a-e are prepared in liquid sample containers 70a-70e, respectively. Components each of which generates ions having different mass-to-charge ratio from each other are dissolved in those reference liquid samples, respectively.

A nebulizer gas passage 41 extending from a nitrogen gas cylinder (nebulizer gas source) 40 is connected to the ESI probe 212 provided in the ionization chamber 21. In the nebulizer gas passage 41, a valve 42 and a branching unit 43 are provided in the mentioned order from the nitrogen gas cylinder 40. A liquid-supply-gas passage 50 is connected to the branching unit 43. The liquid-supply-gas passage 50 is provided with a regulator 51 and a branching unit 52. A relief passage 54 leading to a relief valve 53 is connected to the branching unit 52.

The liquid-supply-gas passage 50 is branched into five liquid-supply-gas sub-passages 50a-50e. The ends of the liquid-supply-gas sub-passages 50a-50e are respectively connected led to the spaces above the liquid levels in the containers (liquid sample containers) 70a-70e each of which contains a reference liquid sample. An atmospheric open passage 56 leading to an atmospheric open valve 55 is provided parallel to the liquid-supply-gas sub-passages 50a-50e.

Additionally, a reference sample supply passage 60 is connected to the ESI probe 212. The other end of the reference sample supply passage 60 is connected to the main port 61g of a six-position seven-way valve 61. The six-position seven-way valve 61 has six sub-ports 61a-61f. One of the sub-ports 61a-61f can be selectively connected to the main port 61g. One end of each of the sample supply sub-passages 60a-60e is connected to each of the sub-ports 61a-61e. The other ends of the sample supply sub-passages 60a-60e are respectively led to the spaces below the liquid levels (i.e. submerged in the liquid) in the liquid sample containers 70a-70e. One end of an atmospheric open passage 62 is connected to the sub-port 61f. The other end of the atmospheric open passage 62 is open to the atmosphere. When the main port 61g is connected to the sub-port 61f, the standard sample supply passage 60 is opened to the atmosphere, and the supply of the reference liquid sample is discontinued. Meanwhile, the supply of the nebulizer gas to the ESI probe 212 is continued. This produces the effect of constantly maintaining the pressure and the state of gas stream inside the ionization chamber 21, thereby preventing unfavorable conditions, such as the fluctuation of the efficiency of the ionization of the liquid sample as the analysis target introduced from the liquid chromatograph unit 1.

Each section of the liquid sample introduction mechanism 3 operates as follows:

Nitrogen gas is supplied from the nitrogen gas cylinder 40 into the nebulizer gas passage 41, for example, at a flow rate of 3 L/min and with a pressure of +500 kPa, where L is the length of the passage from the ESI probe 212 to the valve 42. The notation of "+500 kPa" means that the pressure concerned is higher than the pressure in the ionization chamber 21 (101.325 kPa) by 500 kPa.

The nitrogen gas flowing from the branching unit 43 into the liquid-supply-gas passage 50 is sent through the liquid-sending-gas sub-passage 50a-50e to the liquid sample containers 70a-70e after its pressure is reduced to +100 kPa, for example, by the regulator 51. Thus, the pressure of the liquid-supply gas is regulated independently of the pressure of the nebulizer gas, and the amount of supply of the liquid sample is appropriately changed. The liquid-supply gas simultaneously increases the pressure in all liquid sample containers 70a-70e, whereby the reference liquid samples respectively contained in the liquid sample containers 70a-70e are pushed into the sample supply sub-passages 60a-60e, respectively. If the gas pressure in the liquid-supply-gas passage 50 has excessively increased (e.g. to a level of +150 kPa or higher) due to a problem with the regulator 51, the relief valve 53 is opened to release the nitrogen gas.

During a measurement of a liquid sample to be analyzed, a reference liquid sample (e.g. reference liquid sample "a" contained in the liquid sample container 70a) supplied to one of the sub-ports (sub-port 61a) flows through the main port 61g into the reference sample supply passage 60 and is introduced into the ESI probe 212. The passage in the six-position seven-way valve 61 is sequentially changed by an analysis controller 93 (which will be described later) so that a reference liquid sample to be used in each analysis will be introduced.

In the liquid sample introduction mechanism 3 used in the present embodiment, a portion of the nebulizer gas is introduced into the liquid sample containers 70a-70e, and the reference liquid samples in the liquid sample containers 70a-70e is sent to the ESI probe 212 by the pressure of this nebulizer gas. Therefore, it is unnecessary to provide a supply source of the liquid-supply gas to send the reference liquid samples to the ESI probe 212. Such a system has the advantage of being capable of ionizing the liquid sample at a low cost.

The analyzing operations of the liquid chromatograph unit 1, mass spectrometer unit 2 and liquid sample introduction mechanism 3 are controlled by a control unit 90. The control unit 90 includes an analysis condition setter 92 and analysis controller 93 as its functional blocks, in addition to the storage section 91. The control unit 90 is actually a personal computer on which the necessary software is installed. An input unit 94 and display unit 95 are connected to the control unit.

An analyzing operation of the liquid sample analyzing system in the present embodiment is hereinafter described, using an example in which a plurality of liquid samples as the analysis target are successively analyzed. Each liquid sample to be analyzed is separated into components by the column 14 of the liquid chromatograph unit 1. These components are introduced into the ESI probe 211 of the mass spectrometer unit 2 and ionized. The generated ions are detected by the ion detector 244 along with (the ions of) a reference liquid sample which is introduced from the liquid sample introduction mechanism 3 into the ESI probe 212 and ionized. In the following description, the liquid sample to be analyzed is appropriately called the "target sample", while the reference liquid sample is called the "reference sample".

In advance of the execution of the continuous analysis, the user enters, from the input unit 94, the analysis conditions in the liquid chromatograph unit 1, the analysis conditions in the mass spectrometer unit 2, and the analysis conditions in the liquid sample introduction mechanism 3, for each of the target samples.

The analysis conditions in the liquid chromatograph unit 1 include, for example, measurement conditions, such as the kind, mixture ratio and flow rate of the mobile phases, as well as the conditions concerning the peak detection and peak-list creation processes for a chromatogram created from measurement data.

The analysis conditions in the mass spectrometer 2 include, for example, the measurement mode (e.g. the scan measurement, selected ion monitoring (SIM) measurement, multiple reaction monitoring (MRM) measurement, etc.) and the necessary parameters for that measurement mode (e.g. the mass-scan range and mass-scan rate in the case of the scan measurement, or the mass-to-charge ratios to be selected in the case of the SIM or MRM measurement). The processing conditions concerning the mass calibration of the measurement data as well as the peak detection and peak-list creation processes for a mass spectrum created from measurement data, are also included in the analysis conditions.

The analysis conditions in the liquid sample introduction mechanism 3 include, for example, the kind and flow rate of the reference sample to be used.

The following description deals with the case where a gradient analysis in which a measurement is conducted with the mixture ratio of the mobile phases gradually changed is performed for each target sample in the liquid chromatograph unit 1 to separate the components in the target sample, and the ions generated from those components are subjected to a product ion scan measurement to obtain three-dimensional chromatogram data.

When the analysis conditions mentioned earlier have been entered by the user, the analysis condition setter 92 sets the analysis conditions of the liquid chromatograph unit 1 and the mass spectrometer unit 2 for each liquid sample (i.e. for each analysis), describes those conditions in a method file, and stores this file in the storage section 91. As for the analysis conditions of the liquid sample introduction mechanism 3, the analysis condition setter 92 sets a series of analysis conditions in the continuous analysis, describes those analysis conditions in a method file, and stores this file in the storage section 91.

The use of the method files which describe the analysis conditions, and the preparation of a separate method file for each analysis as regards the liquid chromatograph unit 1 and the mass spectrometer unit 2, are not always required in the present invention. However, there are many measurement parameters and other kinds of parameters used in the liquid chromatograph unit 1 and the mass spectrometer unit 2. If all parameters related to the analyses of a plurality of target samples are compiled into a single file, a considerable amount of time may be needed to read the file. Accordingly, as for the analysis conditions in the liquid chromatograph unit 1 and the mass spectrometer unit 2, it is preferable to prepare one method file for each analysis as in the present embodiment and read the corresponding file at the beginning of each analysis for its execution.

As for the liquid sample introduction mechanism 3, the information related to the kind of reference liquid sample (i.e. the information related to the switching of the passage in the six-position seven-way valve 61) is basically the only parameter that will be changed; the other parameters are fixed in many cases. Therefore, even if the conditions for a plurality of analyses are described in a single method file, it is unlikely that a considerable amount of time is needed to read the file. Accordingly, the analysis conditions concerning the entire series of analyses may be read at the beginning of the first analysis.

When a command to initiate the analysis is issued by the user, the analysis controller 93 reads the method file which describes the conditions of the analysis of the first target sample in the liquid chromatograph unit 1 and the mass spectrometer unit 2, as well as the method file which describes the entire series of analysis conditions in the liquid sample introduction mechanism 3 (reading of the method files).

Subsequently, the analysis controller 93 makes each section of the liquid chromatograph unit 1 and the mass spectrometer unit 2 shift into the state for initiating the measurement. Concurrently, the analysis controller 93 switches the passage in the liquid sample introduction mechanism 3 to introduce a reference sample to be used in the analysis of the first target sample into the ESI probe 212 (pre-measurement step). In this step, it takes approximately one second for the liquid sample introduction mechanism 3 to operate the six-position seven-way valve 61, and approximately ten seconds for the reference sample in the sample supply sub-passage to flow from the six-position seven-way valve 61 to the ESI probe 212 through the reference sample supply passage 60. On the other hand, the liquid chromatograph unit 1 and the mass spectrometer unit 2 complete their pre-measurement steps within a shorter period of time and wait for the completion of the pre-measurement step in the liquid sample introduction mechanism 3 (waiting time). In the present embodiment, for ease of description, it is assumed that the liquid chromatograph unit 1 and the mass spectrometer unit 2 both require the same length of time for their pre-measurement steps as well as for their post-measurement steps (which will be described later). If one of these two units requires a longer period of time, the other unit waits for the first unit to complete its operation.

After all pre-measurement steps have been completed in the liquid chromatograph unit 1, mass spectrometer unit 2 and liquid sample introduction mechanism 3, a target sample is introduced into the injector 13 of the liquid chromatograph unit 1, and the measurement is initiated. As described earlier, the target sample introduced from the injector 13 is separated into components by the column 14. Those components are introduced into the ESI probe 211 and ionized. The generated ions, along with the ions of the reference sample introduced into the ESI probe 212 of the liquid sample introduction mechanism 3, undergo mass separation and are detected by the ion detector 244. The output signals from the ion detector 244 are sequentially sent to the control unit 90 and stored in the storage section 91 (measurement step).

After the measurement of the target sample has been completed, the analysis controller 93 reads the measurement data stored in the storage section 91, creates three-dimensional chromatogram data formed by the three axes of time, mass-to-charge ratio and ion intensity, and adds a header for identifying the analysis. Subsequently, the analysis controller 93 detects peaks in the chromatogram and creates a peak list. It also performs mass calibration of the mass spectrum, detects mass peaks and creates a peak list (post-measurement step 1).

In parallel with the previously described data processing, an equilibrating process for the column 14 is performed in the liquid chromatograph unit 1. Specifically, the column 14 which is filled with the mobile phase at the mixture ratio at the end of the gradient analysis is replenished with a mobile phase at a normal mixture ratio, and the column 14 is equilibrated (post-measurement step 2).

Figure 3A:
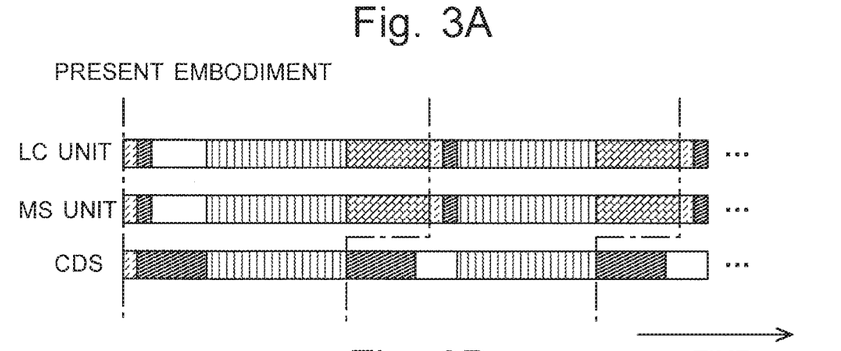
FIGS. 3A and 3B are diagrams illustrating the flow of the analyzing operation in the present embodiment in comparison with a conventional example.

In the liquid sample analysis system according to the present embodiment, the pre-measurement step for operating the six-position seven-way valve 61 to introduce a reference sample to be used in the next analysis into the ESI probe 212 is performed in the liquid sample introduction mechanism 3 in parallel with the previously described post-measurement steps related to the liquid chromatograph unit 1 and the mass spectrometer unit 2 (FIG. 3A). In the liquid chromatograph unit 1 and the mass spectrometer unit 2, the operation of reading the method file for the analysis of the next target sample and the pre-measurement step are successively performed after the post-measurement step for the analysis of the first target sample has been completed. Upon completion of all pre-measurement steps in the liquid chromatograph unit 1, mass spectrometer unit 2 and liquid sample introduction mechanism 3, the target sample is introduced into the injector 13 and the measurement is initiated. After the completion of this measurement step, the post-measurement steps in the liquid chromatograph unit 1 and the mass spectrometer unit 2 are once more performed, while the pre-measurement step for the next analysis is concurrently performed in the liquid sample introduction mechanism 3. The steps described thus far are subsequently repeated until the analyses of all target samples are completed.

Figure 3B:
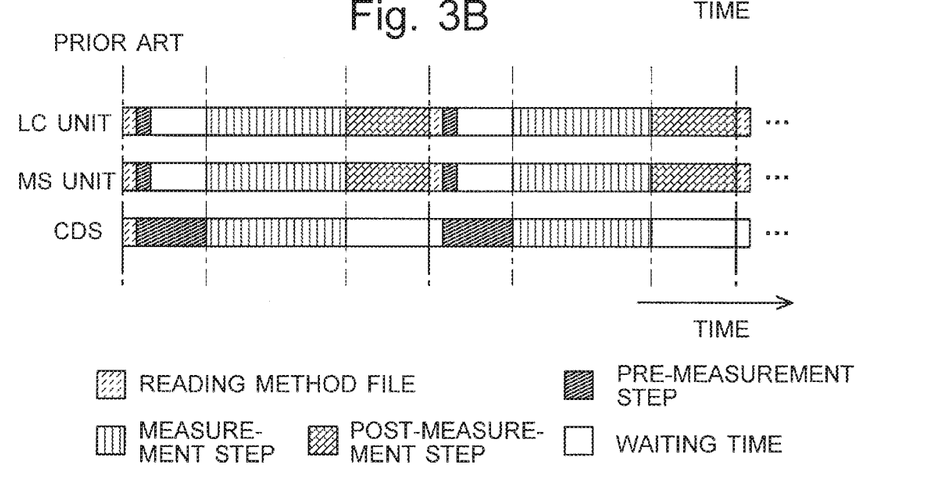

In the case of a conventional liquid sample analysis system the liquid sample introduction mechanism 3 stands by, with the reference sample used in the just-completed measurement still retained in the ESI probe 212, until the post-measurement steps related to the liquid chromatograph unit 1 and the mass spectrometer unit 2 are completed. After the post-measurement steps for the liquid chromatograph unit 1 and the mass spectrometer unit 2 have been completed, and the subsequent reading of the method file which describes the analysis conditions in the liquid chromatograph unit 1 and the mass spectrometer unit 2 has also been completed, the pre-measurement step in the liquid sample introduction mechanism 3 (the operation of the six-position seven-way valve 61 to introduce the reference liquid sample for the next analysis into the ESI probe 212) is performed in parallel with the pre-measurement steps in the liquid chromatograph unit 1 and the mass spectrometer unit 2. Specifically, as shown in FIG. 3B, the pre-measurement steps and the measurement steps are each simultaneously initiated in the liquid chromatograph unit 1, mass spectrometer unit 2, and liquid sample introduction mechanism 3, whereas the liquid sample introduction mechanism 3 is made to stand by while the post-measurement steps related to the liquid chromatograph unit 1 and the mass spectrometer unit 2 are being performed.

In a liquid chromatograph mass spectrometer, the post-measurement step normally requires a longer period of time than the pre-measurement step. As just described, this period of time has conventionally been a waiting time in the liquid sample introduction mechanism 3. On the other hand, the step which primarily requires time in the liquid sample introduction mechanism 3 is the pre-measurement step (the operation of introducing a reference liquid sample into the ESI probe 212). Most of this period of time has conventionally been a waiting time in the liquid chromatograph unit 1 and the mass spectrometer unit 2. By comparison, in the present embodiment, the time-consuming operations in the liquid chromatograph unit 1 and the mass spectrometer unit 2 are performed in parallel with the time-consuming operation in the liquid sample introduction mechanism 3. The waiting time in each of those units is thereby reduced, so that the analyzing time is reduced, and the throughput of the analysis is enhanced.

Figure 4:
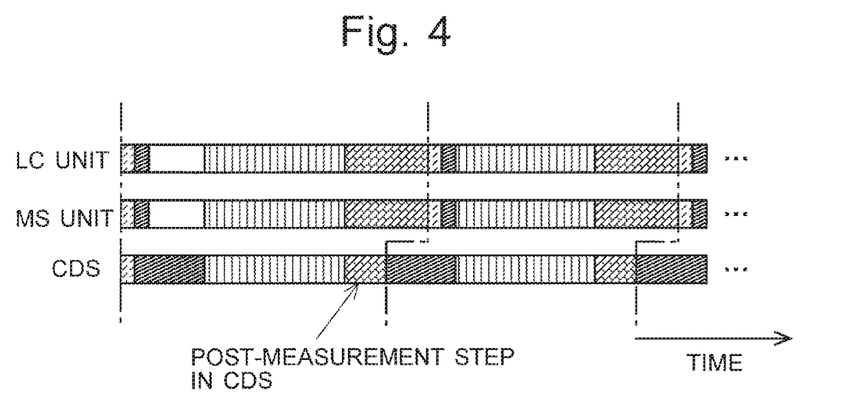
FIG. 4 is a diagram illustrating another example of the flow of the analyzing operation in the present embodiment.

In the previously described embodiment, no post-measurement step is performed in the liquid sample introduction mechanism 3. However, in some cases, a post-measurement step may be performed. For example, in the case of equilibrating the column 14 in the liquid chromatograph unit 1 or cooling the column 14 to a predetermined temperature after the temperature of the column 14 has been gradually increased during the measurement, a long period of time is required for the post-measurement step (e.g. equilibrating or cooling the column 14 may take several minutes). In such a case, a post-measurement step in which the sub-port 61*f* of the six-position seven-way valve 61 is connected to the main port 61*g* for a predetermined period of time (e.g. for a period of time which is equal to the equilibrating or cooling time of the column in the liquid chromatograph unit 1 from which the time for the subsequent pre-measurement step is subtracted) may be performed in the liquid sample introduction mechanism 3 before the pre-measurement step for the next analysis is initiated (FIG. 4). By this post-measurement step, the supply of the reference liquid is suspended, and unnecessary consumption of the reference liquid sample is prevented.

Figure 5:
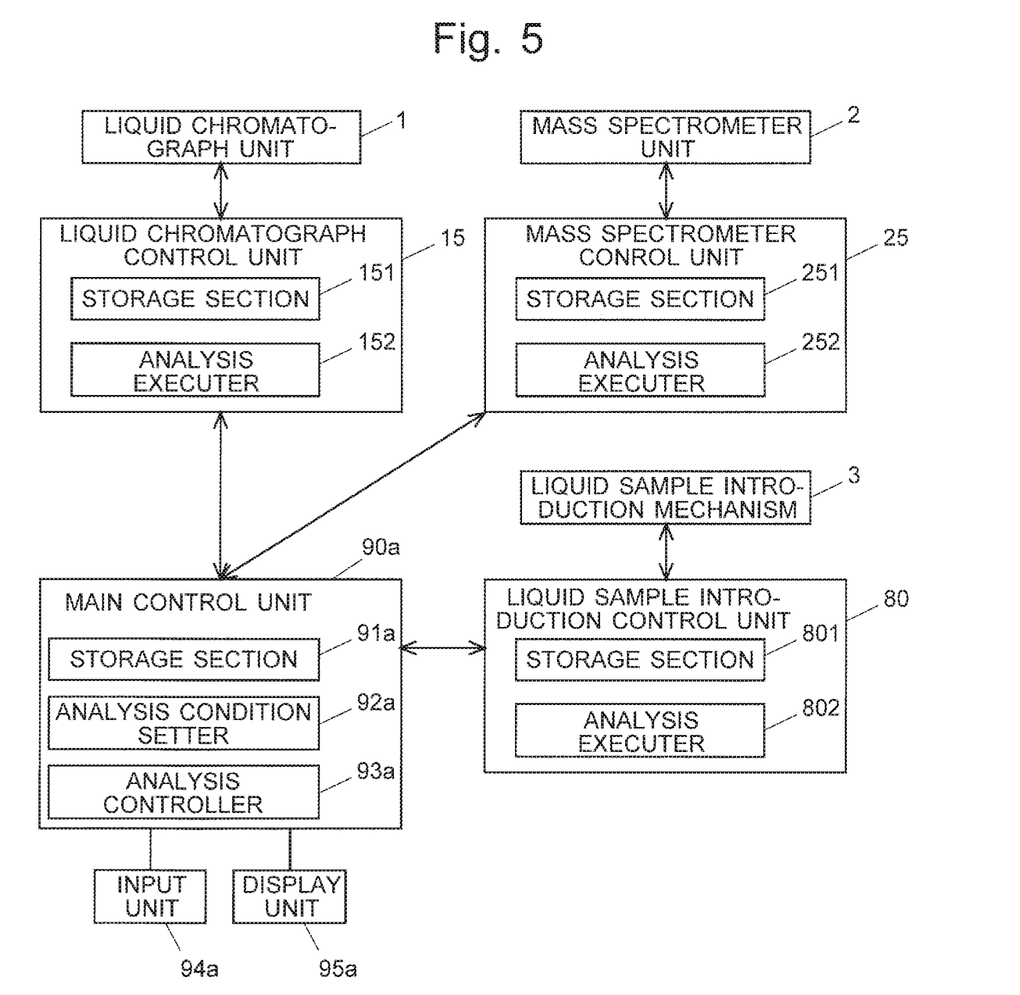
FIG. 5 is a configuration diagram of the main components in a variation of the liquid sample analyzing system according to the present invention.

In the previous embodiment, the single analysis controller 93 controls the analyzing operations of the liquid chromatograph unit 1, mass spectrometer unit 2, and liquid sample introduction mechanism 3. It is also possible to adopt the configuration in which each unit (or mechanism) is independently provided with a controller. As one such example, FIG. 5 shows the configuration of the main components in a variation of the embodiment.

The system in the present variation includes: a liquid chromatograph control unit 15 for controlling the analyzing operations of each section of the liquid chromatograph unit 1; a mass spectrometer control unit 25 for controlling the analyzing operations of each section of the mass spectrometer unit 2; and a liquid sample introduction control unit 80 for controlling the analyzing operations of each section of the liquid sample introduction mechanism 3. Each control unit includes a storage section 151, 251 or 801 as well as an analysis executer 152, 252 or 802. The liquid chromatograph control unit 15, mass spectrometer control unit 25 and liquid sample introduction control unit 80 operate under the control of an analysis controller 93a in the main control unit 90a.

Operations by the user, such as the entry of the analysis conditions, are performed through an input unit 94a connected to the main control unit 90a. Analysis results and other related information are shown on the screen of a display unit 95a.

An analyzing operation in the present variation is hereinafter described. The following descriptions mainly deals with the characteristic operations of the present variation. Descriptions of the operations similar to the previous embodiment will be appropriately omitted.

After the analysis conditions mentioned earlier have been entered by the user, the analysis condition setter 92a prepares a method file which describes the analysis conditions of the liquid chromatograph unit 1 and the mass spectrometer unit 2 for each liquid sample (i.e. for each analysis), and stores this file in the storage section 91a. As for the analysis conditions of the liquid sample introduction mechanism 3, the analysis condition setter 92a prepares a method file which describes a series of analysis conditions in the continuous analysis, and stores this file in the storage section 91a.

When a command to initiate the analysis is issued by the user, the analysis executer 152 in the liquid chromatograph control unit 15 under the command of the analysis control unit 93a reads the method file which describes the conditions of the analysis of the first target sample in the liquid chromatograph unit 1, and performs a pre-measurement step. The analysis executer 252 in the mass spectrometer control unit 25 also performs a pre-measurement step by a similar procedure. The analysis executer 802 in the liquid sample introduction control unit 80 reads, from the storage section 91a, a method file which describes a series of analysis conditions for the analyses of a plurality of target samples, stores this file in the storage section 801 in the liquid sample introduction control unit 80, and performs a pre-measurement step for the analysis of the first target sample.

After the pre-measurement steps in the liquid chromatograph unit 1, mass spectrometer unit 2, and liquid sample introduction mechanism 3 have been completed, these units and mechanism simultaneously initiate the measurement of the target sample. The measurement data obtained in the mass spectrometer unit 2 are stored in the storage section 251. If the liquid chromatograph unit 1 includes a detector, such as an absorptiometer, measurement data are also obtained in the liquid chromatograph unit 1 and stored in the storage section 151.

After the measurement step in the liquid chromatograph unit 1, mass spectrometer unit 2, and liquid sample introduction mechanism 3 have been completed, the post-measurement steps are performed in the liquid chromatograph unit 1 and the mass spectrometer unit 2, respectively, while the pre-measurement step for the analysis of the next target sample is concurrently performed in the liquid sample introduction mechanism 3. The measurement data which have been subjected to the predetermined processing in the liquid chromatograph unit 1 and the mass spectrometer unit 2 may be temporarily stored in the respective storage sections 151 and 251, to be transferred to the storage section 91a in the main control unit 90a after the completion of the entire series of analyses. Alternatively, those data may be transferred to the storage section 91a in the main control unit 90a at the end of the post-measurement step in each analysis. In the latter case, although the period of time for the post-measurement step becomes longer due to the transfer of the measurement data, there is the advantage that the user can make the chromatogram or mass spectrum be presented on the display unit 95a to visually check it as needed before the completion of the entire series of analyses. The previously described operations are subsequently repeated until the entire series of analyses is completed.

Any of the previous embodiments is one example of the present invention. Their configuration or analyzing operation can be appropriately changed within the spirit of the present invention.

In the previous embodiments, a liquid chromatograph mass spectrometer has been used as one example of the ion analyzer. A similar system can be constructed for various types of ion analyzers, such as a normal mass spectrometer (i.e. a mass spectrometer in which the target sample is directly introduced into the ESI probe 211) or ion mobility spectrometer. The specific contents of the pre-measurement steps and the post-measurement steps in the previous embodiment are mere examples presented on the assumption that a liquid chromatograph mass spectrometer is used. Appropriate operations should be performed according to the kind of ion analyzers, purpose of the analysis and other related factors.

REFERENCE SIGNS LIST

1 . . . Liquid Chromatograph Unit
   10a, 10b . . . Mobile Phase Container
   11 . . . Mixer
   12 . . . Pump
   13 . . . Injector
   14 . . . Column
   15 . . . Liquid Chromatograph Control Unit
      151 . . . Storage Section
      152 . . . Analysis Executer
2 . . . Mass Spectrometer Unit
   21 . . . Ionization Chamber
      211, 212 . . . ESI Probe
      213 . . . Desolvation Tube
   22 . . . First Intermediate Vacuum Chamber
      221 . . . Ion Guide
      222 . . . Skimmer
   23 . . . Second Intermediate Vacuum Chamber
      231 . . . Ion Guide
   24 . . . Analysis Chamber
      241 . . . Ion Trap
      242 . . . Time-of-Flight Mass Separator (TOF)
         243 . . . Reflectron Electrode
         244 . . . Ion Detector
   25 . . . Mass Spectrometer Control Unit
      251 . . . Storage Section
      252 . . . Analysis Executer
3 . . . Liquid Sample Introduction Mechanism
   40 . . . Nitrogen Gas Cylinder 41 ... Nebulizer Gas Passage
42 ... Valve
43 ... Branching Unit
50 ... Liquid-Supply-Gas Passage
50a~50e ... Liquid-Supply-Gas Sub-Passage
51 ... Regulator
52 ... Branching Unit
53 ... Relief Valve
54 ... Relief Passage
55 ... Atmospheric Open Valve
56 ... Atmospheric Open Passage
60 ... Reference Sample Supply Passage
60a-60e ... Sample Supply Sub-Passage
61 ... Six-Position Seven-Way Valve
62 ... Atmospheric Open Passage
70a-70e ... Liquid Sample Container
80 ... Liquid Sample Introduction Control Unit
   801 ... Storage Section
   802 ... Analysis Executer
90, 90a ... Control Unit
   91, 91a ... Storage Section
   92, 92a ... Analysis Condition Setter
   93, 93a ... Analysis Controller
   94, 94a ... Input Unit
   95, 95a ... Display Unit

The invention claimed is:

1. A liquid sample analyzing system used for continuously performing analyses of a plurality of liquid samples, the liquid sample analyzing system comprising:
a liquid chromatograph;
a mass spectrometer including a first ion source into which a target liquid sample to be analyzed is introduced and a second ion source into which one of a plurality of reference liquid samples is introduced;
a reference liquid sample introduction mechanism including a passage-switching section for selectively introducing the one of the plurality of reference liquid samples into the second ion source; and
a control unit configured to perform a series of steps, the series of steps including:
a pre-measurement step of making each section of the liquid chromatograph shift into a state for initiating a first measurement;
a first measurement step of introducing the target liquid sample to be analyzed into the first ion source and performing a measurement on an ion originating from the target liquid sample along with an ion originating from a first reference liquid sample introduced into the second ion source by the reference liquid sample introduction mechanism; and
a concurrent operation step that includes concurrently operating the liquid chromatograph to perform a predetermined post-measurement-completion process and operating the reference liquid sample introduction mechanism to perform a pre-second measurement switching step concurrently with the predetermined post-measurement-completion process, the pre-second measurement switching step including operating the reference liquid sample introduction mechanism so as to switch the passage-switching section from a first passage to a second passage through which a second reference liquid sample to be used in a subsequent second measurement is introduced.

2. The liquid sample analyzing system according to claim 1, wherein, after the first measurement step, the control unit operates the reference liquid sample introduction mechanism to perform a post-measurement step of discontinuing an introduction of the first reference liquid sample, before an introduction of the second reference liquid sample to be used in the second measurement.

3. The liquid sample analyzing system according to claim 1, wherein
the passage-switching section comprises one main port and a plurality of sub-ports to be selectively connected to the main port; and
the reference liquid sample introduction mechanism further comprises:
a nebulizing-gas passage that supplies a nebulizing gas to the second ion source;
a plurality of liquid sample containers that hold the plurality of reference liquid samples, where each of the liquid sample containers is a hermetically closed container;
a liquid-supply-gas passage with one end connected to an intermediate portion of the nebulizing-gas passage and another end branched into sub-passages each of which is connected to a space above a liquid level in one of the plurality of liquid sample containers;
the sample-supply main passage with one end connected to the second ion source and another end connected to the main port; and
a sample-supply sub-passage including a plurality of passages each of which has one end connected to a space below the liquid level in one of the liquid sample containers and another end connected to one of the plurality of sub-ports.

4. The liquid sample analyzing system according to claim 3, wherein one of the sub-ports is open to atmosphere.

5. The liquid sample analyzing system according to claim 3, wherein the reference liquid sample introduction mechanism further comprises a liquid-supply-gas pressure regulator that regulates a pressure of gas flowing through the liquid-supply-gas passage independently of a pressure of the nebulizing gas supplied to the second ion source.

6. The liquid sample analyzing system according to claim 1, wherein the control unit repeats the series of steps.

7. The liquid sample analyzing system according to claim 1, wherein the predetermined post-measurement-completion process includes at least one of: adding a header for identifying the measurement to obtained data and storing the obtained data in a predetermined file format.

8. The liquid sample analyzing system according to claim 1,
wherein the predetermined post-measurement-completion process includes a predetermined processing on measurement data that is obtained in the first measurement step.

9. The liquid sample analyzing system according to claim 8,
wherein the predetermined processing includes (i) at least one of detecting a peak of a chromatogram and creating a peak list or (ii) an equilibrating process for a column of the liquid chromatograph.

10. A liquid sample analyzing system used for continuously performing analyses of a plurality of liquid samples, the liquid sample analyzing system comprising:
a liquid chromatograph;
a mass spectrometer including a first ion source into which a target liquid sample to be analyzed is introduced and a second ion source into which one of a plurality of reference liquid samples is introduced;

a reference liquid sample introduction mechanism including a passage-switching section for selectively introducing the one of the plurality of reference liquid samples into the second ion source; and a control unit configured to perform a series of steps and control the liquid chromatograph, the mass spectrometer and the reference liquid sample introduction mechanism, wherein the control by the control unit includes controlling the three devices and the controlling includes a pre-measurement step, a measurement step, and a concurrent post-measurement and switching step that performs a post-measurement step for performing a predetermined post-measurement-completion process and where the reference liquid sample introduction mechanism is operated concurrently with the predetermined post-measurement step so as to switch the passage-switching section to a passage through which a reference liquid sample to be used in a next analysis is introduced.

11. The liquid sample analyzing system according to claim 10, wherein the predetermined post-measurement-completion process includes at least one of: adding a header for identifying the measurement to obtained data and storing the obtained data in a predetermined file format.

12. The liquid sample analyzing system according to claim 10, wherein the predetermined post-measurement-completion process includes a predetermined processing on measurement data that is obtained in the first measurement step.

13. The liquid sample analyzing system according to claim 12, wherein the predetermined processing includes (i) at least one of detecting a peak of a chromatogram and creating a peak list or (ii) an equilibrating process for a column of the liquid chromatograph.

\* \* \* \* \*